US011938490B2

(12) United States Patent
Murray et al.

(10) Patent No.: US 11,938,490 B2
(45) Date of Patent: Mar. 26, 2024

(54) MAGNETIC SEPARATION

(71) Applicant: FERROLOGIX, INC., Valencia, CA (US)

(72) Inventors: Coleman Murray, Valencia, CA (US); Tim Tiemann, Valencia, CA (US)

(73) Assignee: FERROLOGIX, INC., Valencia, CA (US)

( * ) Notice: Subject to any disclaimer, the term of this patent is extended or adjusted under 35 U.S.C. 154(b) by 0 days.

(21) Appl. No.: 17/589,240

(22) Filed: Jan. 31, 2022

(65) Prior Publication Data

US 2022/0241797 A1 Aug. 4, 2022

Related U.S. Application Data

(60) Provisional application No. 63/145,806, filed on Feb. 4, 2021.

(51) Int. Cl.
| | |
|---|---|
| *B03C 1/03* | (2006.01) |
| *B01L 3/00* | (2006.01) |
| *B01L 3/02* | (2006.01) |
| *B03C 1/033* | (2006.01) |
| *B03C 1/23* | (2006.01) |
| *B03C 1/28* | (2006.01) |
| *C12N 13/00* | (2006.01) |
| *G01N 1/40* | (2006.01) |
| *G01N 15/10* | (2006.01) |
| *G01N 35/00* | (2006.01) |

(52) U.S. Cl.
CPC .............. *B03C 1/03* (2013.01); *B03C 1/0332* (2013.01); *B03C 1/0335* (2013.01); *B03C 1/288* (2013.01); *C12N 13/00* (2013.01); *B03C 2201/18* (2013.01); *B03C 2201/22* (2013.01); *B03C 2201/26* (2013.01); *G01N 2015/1006* (2013.01); *G01N 2015/1081* (2013.01)

(58) Field of Classification Search
CPC ...... B03C 1/03; B03C 1/0332; B03C 2201/22
USPC ............................................. 209/215
See application file for complete search history.

(56) References Cited

U.S. PATENT DOCUMENTS

| | | | |
|---|---|---|---|
| 11,273,454 B2 | 3/2022 | Kilinc et al. | |
| 2008/0302732 A1* | 12/2008 | Soh | B03C 1/015 210/695 |
| 2009/0159511 A1 | 6/2009 | Molteni | |
| 2010/0078362 A1 | 4/2010 | Riise et al. | |

(Continued)

OTHER PUBLICATIONS

Murray, Coleman Tyler, UCLA Electronic Theses and Dissertations, Micromagnetic Ratcheting Manipulation for Bioengineering Research Applications, https://escholarship.org/uc/item/4vx4d586, 2015, 109 pages.

(Continued)

*Primary Examiner* — Michael McCullough
*Assistant Examiner* — Molly K Devine
(74) *Attorney, Agent, or Firm* — Perkins Coie LLP

(57) ABSTRACT

A system for separating particles or cells by magnetic ratcheting has a vector of spaced apart magnetic bars on a substrate. The system can be used to separate and concentrate magnetic objects based on iron oxide content. For cells, different phenotypes may be separated based on surface expression of proteins or molecules that are bound to magnetic beads. A magnetic field generator generates a cycling magnetic field that acts to separate magnetic particles or cells from non-magnetic particles or cells in a solution.

19 Claims, 23 Drawing Sheets

(56) References Cited

U.S. PATENT DOCUMENTS

| | | |
|---|---|---|
| 2011/0168618 A1 | 7/2011 | Danov et al. |
| 2011/0212440 A1 | 9/2011 | Viovy et al. |
| 2013/0264248 A1 | 10/2013 | Smolkin et al. |
| 2014/0021105 A1 | 1/2014 | Lee et al. |
| 2017/0362563 A1 | 12/2017 | Di Carlo et al. |
| 2019/0143328 A1* | 5/2019 | Savran .................. B03C 1/0335 435/5 |

OTHER PUBLICATIONS

International Search Report and Written Opinion for International Application No. PCT/US2022/014447; dated May 18, 2022; 12 pages.

* cited by examiner

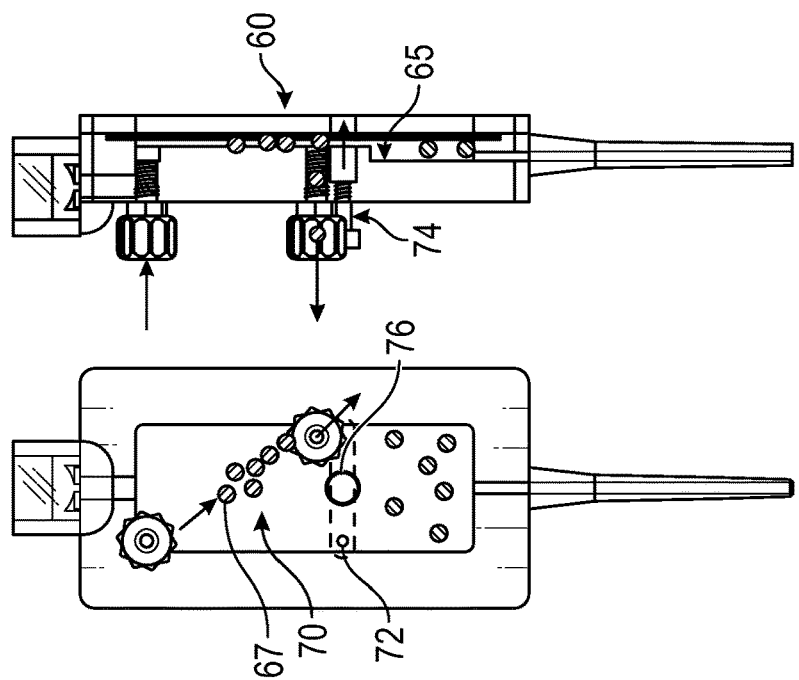
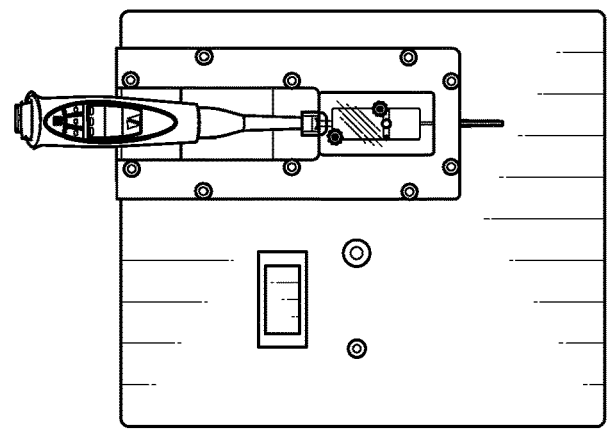
FIG. 5C
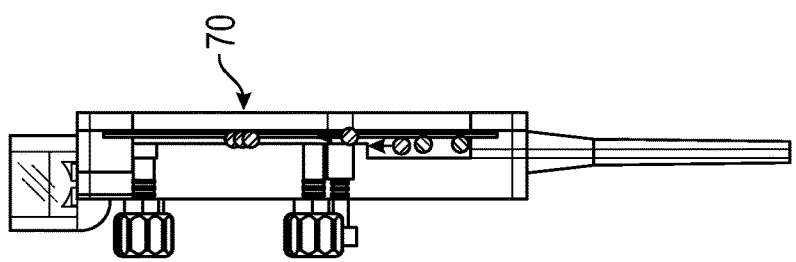
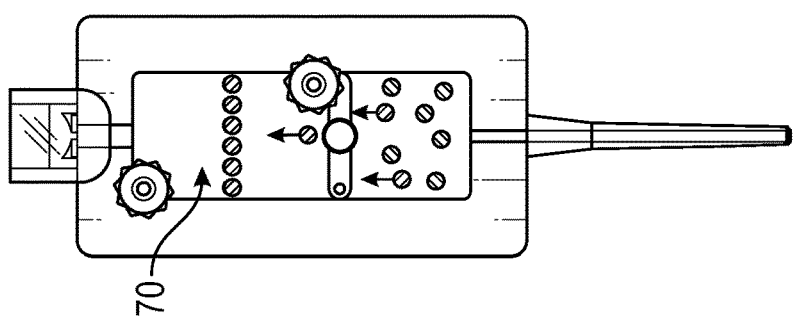

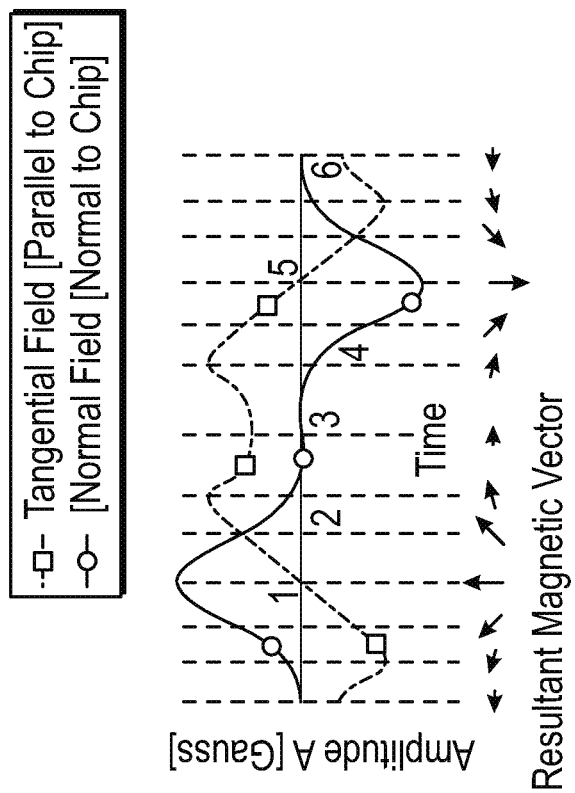
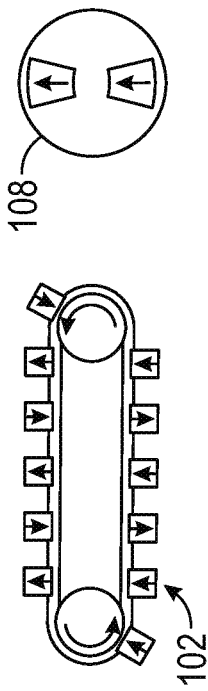
FIG. 15

1D Bar Design

Biases Transport in 1D →

120  150

Pillar Design

MAGNETIC SEPARATION

TECHNICAL FIELD

This application claims priority to U.S. Provisional Patent Application No. 63/145,806 filed Feb. 4, 2021, now incorporated herein by reference. The field of the invention is ferromagnetic methods and apparatus for separating cells and other microscopic particles.

BACKGROUND

In many medical testing and research areas, it is necessary to separate cells from a solution. Magnetic ratcheting is one technique used for this purpose. Magnetic ratcheting operates by binding or incorporating magnetic beads onto or into specific types of cells, biological agents or analytes, thus making them magnetic bodies. A magnetic separating force can then be applied to magnetic bodies, allowing the magnetic bodies to be separated out from the solution. Generally, the magnetic beads are micron-scale or nano-scale particles, e.g., in the range of 5 microns down to about 50-100 nm. Although magnetic ratcheting has achieved varying degrees of success in the past, engineering challenges remain in achieving improved magnetic ratcheting methods and apparatus.

SUMMARY

A system for the magnetic separation of magnetic bodies includes a plurality of ferromagnetic elements spaced apart in a row on a substrate. A support surface is positioned over the vector of ferromagnetic elements and is configured to receive the particles or cells. A magnetic field generator is positioned adjacent to the support surface and may include a rotating wheel having a plurality of permanent magnets arranged in a full radial Halbach array. The magnetic substrate and the rotating magnetic field may have a non-zero angle orientation relative to gravity. The pitch or spacing between the ferromagnetic elements may increase in ascending height on the substrate.

A method for separating cells includes providing magnetic material onto or into the cells while the cells are in a liquid solution, to make the cells magnetic. The solution containing the magnetic bodies is loaded into a substrate. The solution is moved uphill across a plurality of spaced apart magnetic elements. The magnetic elements may be spaced apart to provide progressively increasing pitch zones from a first portion of the substrate towards a second portion of the substrate.

A substrate for use in magnetic separation includes a plurality of magnetic bars on a glass component. The spacing between adjacent magnetic bars increases in a direction along a vector of magnetic bars. The magnetic bars may be grouped into two or more pitch zones with the spacing of the bars increasing linearly in sequential pitch zones. The bars may comprise a metal layer on the glass, with the bars perpendicular to a length of the substrate.

A cartridge for magnetic separation includes a housing having at least one liquid inlet and at least one extraction port. A substrate in the housing has a plurality of ferromagnetic bars spaced apart on the substrate. A support surface is disposed over the ferromagnetic elements. Using a design having two extraction ports, magnetic bodies having different magnetization may be separated at specific pitch ranges.

BRIEF DESCRIPTION OF THE DRAWINGS

In the drawings the same element number indicates the same element in each of the views.

FIG. 5A is a front view of the cartridge of FIGS. 4A and 4B with the solution in the extraction region of the cartridge.

FIG. 5B is a side cross section view of the cartridge shown in FIG. 5A.

FIG. 5C is a front view of the cartridge of FIGS. 4A and 4B inserted into a cartridge receptacle of the apparatus shown in FIGS. 1 and 2.

FIG. 6A is a front view of the cartridge of FIGS. 4A-5B showing extraction of the solution containing magnetized target cells, beads, agents or analytes.

FIG. 6B is a side cross section view of the cartridge shown in FIG. 6A.

FIGS. 14-17 are schematic views of magnetics field which may be used in the apparatus of FIG. 1.

DETAILED DESCRIPTION

Figure 2:
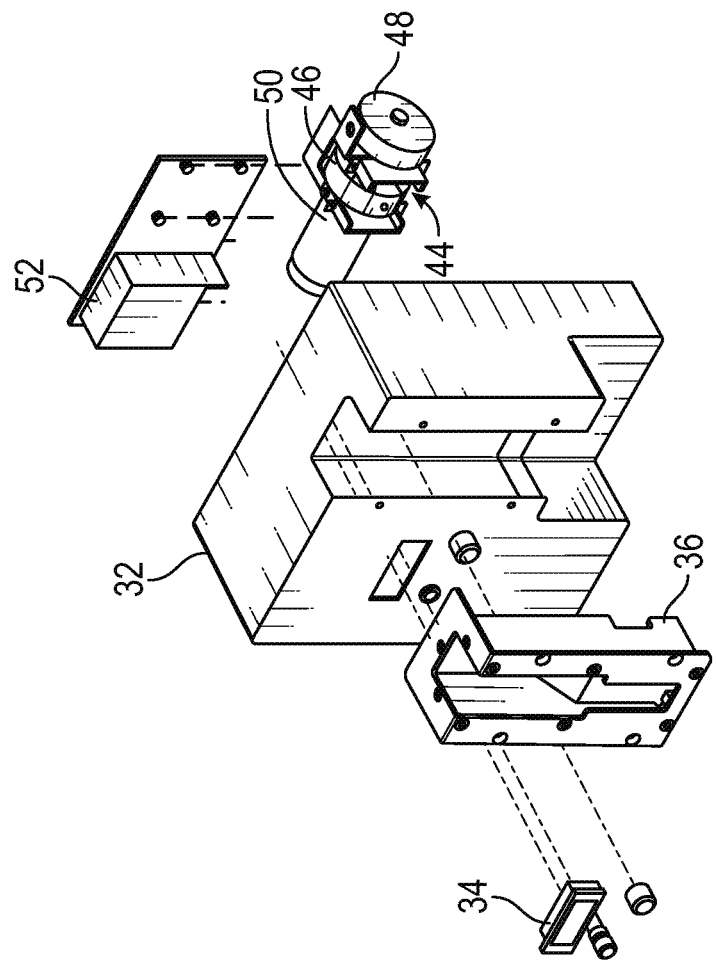
FIG. 2 is an exploded perspective view of the apparatus of FIG. 1.
Figure 1:
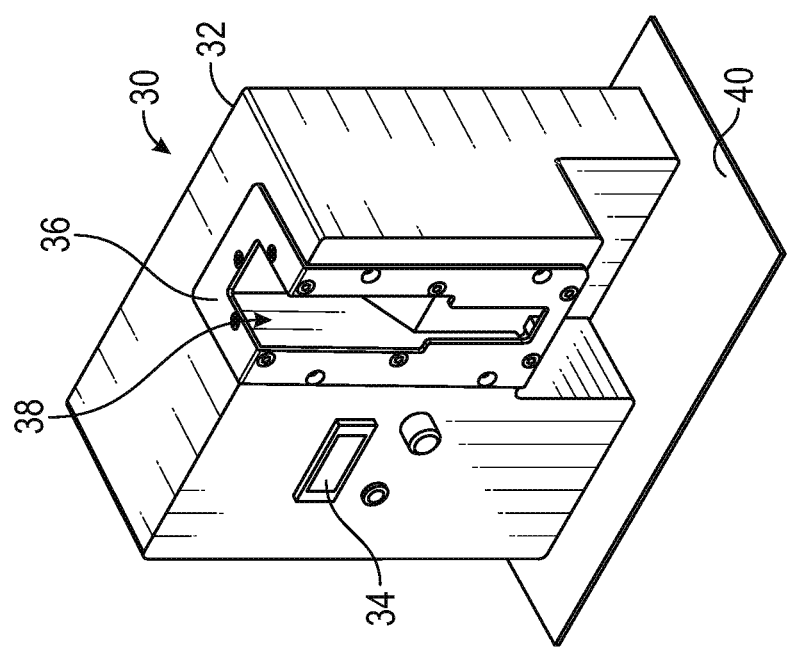
FIG. 1 is a perspective view of a magnetic ratcheting apparatus.

FIGS. 1 and 2 show an example of a novel magnetic ratcheting apparatus having advantages over previous designs. The apparatus or instrument 30 has a cartridge receptacle 36 and may include a display 34 on a front side of a housing 32. A cartridge slot 38 in the cartridge receptacle 36 is adapted to receive a cartridge 60, such as one of the cartridges 60 shown in FIGS. 3-13. The housing 32 may be supported on a tilt platform 40 which allows the orientation of the apparatus 30 to be adjusted, for example from the vertical or upright position shown in FIG. 1 to a horizontal position, as well as any inclination angle between vertical and horizontal. As shown in FIG. 2, the apparatus 30 includes a magnetic field generator 44 for creating a magnetic field used to separate magnetic bodies or cells. The magnetic field generator may be a magnetic wheel assembly having a magnetic wheel 46 rotated by a motor 50. The magnetic wheel 46 may have multiple permanent magnets arranged in a full radial Halbach array. The magnetic field generator 44 may alternatively also be a hybrid electromagnet and rare earth magnetic planar field generator. An rpm sensor 48 and a controller for the motor 50 are electrically connected to a control circuit 52.

Figure 3:
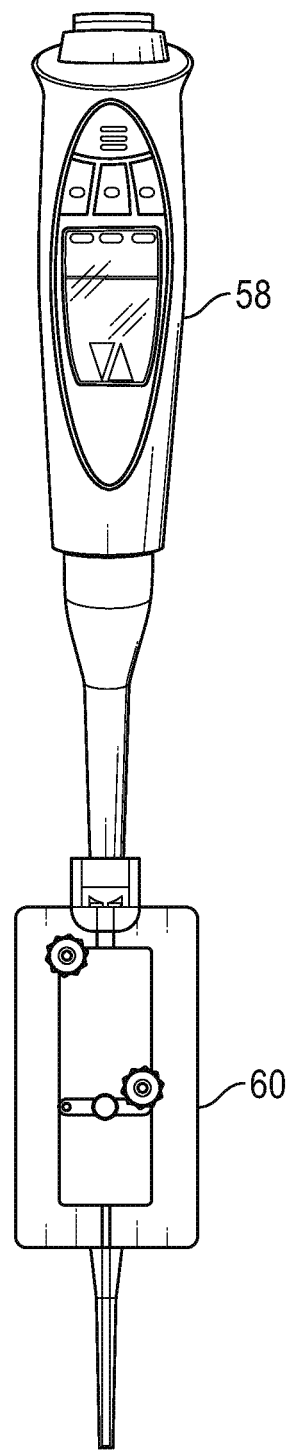
FIG. 3 is a front view of a pipette interfacing with a cartridge to perform fluid pumping operations.
Figure 4A:
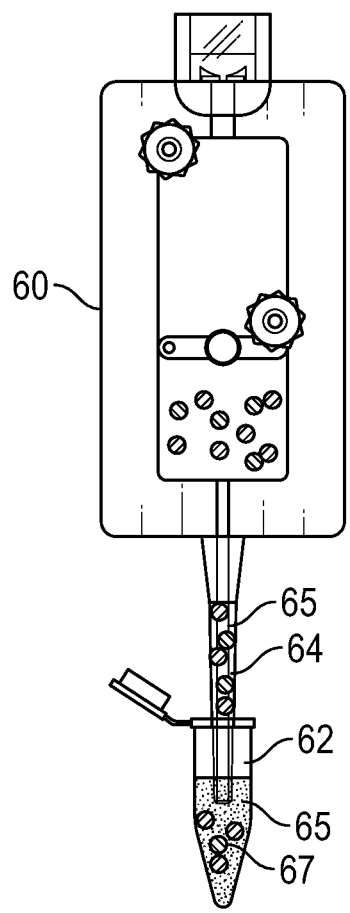
FIG. 4A is a front view of a cartridge drawing in a solution from a container.
Figure 4B:
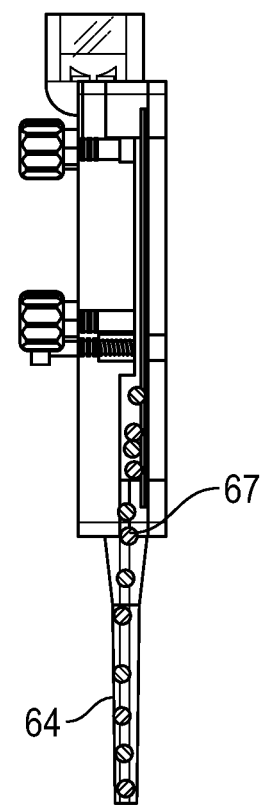
FIG. 4B is a side cross section view of the cartridge of FIG. 4A with the container removed.

In use, a solution containing the magnetic bodies is introduced into a substrate 94 in a cartridge 60, optionally using a pipette 58 as shown in FIG. 3. As used here, magnetic body means a cell or a particle that is or has been made magnetic, in the sense it can be influenced to move by a magnetic field. Alternatively, the solution may be drawn into an inlet 64 at a bottom end of the cartridge 60 as shown in FIGS. 4A and 4B. The solution moves up from the inlet 64 to an extraction region of the cartridge 60, as shown in FIGS. 5A and 5B. FIG. 5C shows the cartridge 60 installed in the cartridge slot 38 of the apparatus 30.

Referring to FIGS. 5A to 6B both magnetic and non-magnetic cells or particles are drawn into the bottom chamber of the cartridge. The pipette or pump draws the entire sample into the cartridge. The magnetic field generator 44 creates a magnetic field which pulls magnetic bodies in the liquid sample onto the surface of a substrate having ferromagnetic bars or microstructures. Non-magnetic bodies will remain in solution in the bottom chamber of the cartridge. As the magnetic field generator 44 produces an oscillatory magnetic field, the magnetic bodies move vertically up the substrate and become trapped in the extraction chamber or region 70. Nonmagnetic particles remain in the bottom chamber of the cartridge.

Figure 4C:
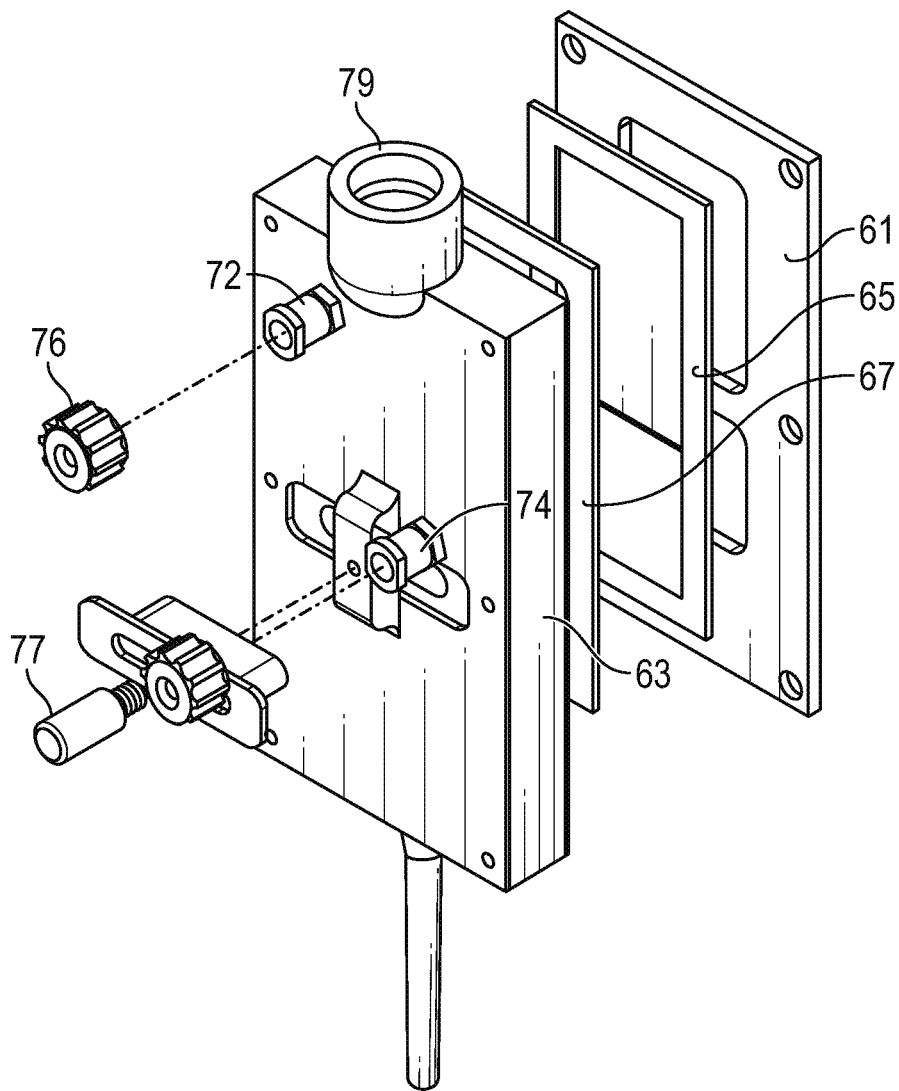
FIG. 4C is a perspective view of the cartridge shown in FIG. 4A.

As shown in FIG. 4C, the cartridge 60 may include a backing plate 61 which may be screwed onto a cartridge body 63 holding a ferromagnetic chip 65 within the cartridge body 63. The ferromagnetic chip 65 may be seated on a gasket or adhesive spacer. A pipette or pump interface fitting 79 is provided at the top of the cartridge body 63. A plunger or lead screw 77 may be used to open and close the extraction port.

As shown in FIGS. 6A and 6B, an extraction gate or lock 72 is then moved into position to close or seal off the extraction region or chamber 70 containing the magnetic bodies from the rest of the solution in the cartridge 60. The extraction gate 72 may be operated by hand, e.g., by pulling or pushing on a knob 76 on the outside of the cartridge 60, causing a gasket to close off a channel within the cartridge. The magnetic bodies 67 can then be extracted from the cartridge 60 via an extraction port 74. Use of the extraction gate 72 provides advantages in the maintenance of purified cell populations. Alternative forms of extraction gates may be used. For example, extraction gates that are electrically operated by the control circuit 52 may be used. Alternatively, magnetic barriers may optionally be used.

The solution containing the non-magnetic bodies remaining in the cartridge is discarded and the cartridge may be cleaned and reused. Alternatively, the cartridge may be designed for single use and discarded after the magnetic bodies are extracted. Single use can provide a potentially aseptic system. The extraction ports 74 are preferably not at the end of a column or row of the magnetic bars or elements of the cartridge, as described below.

Figure 7:
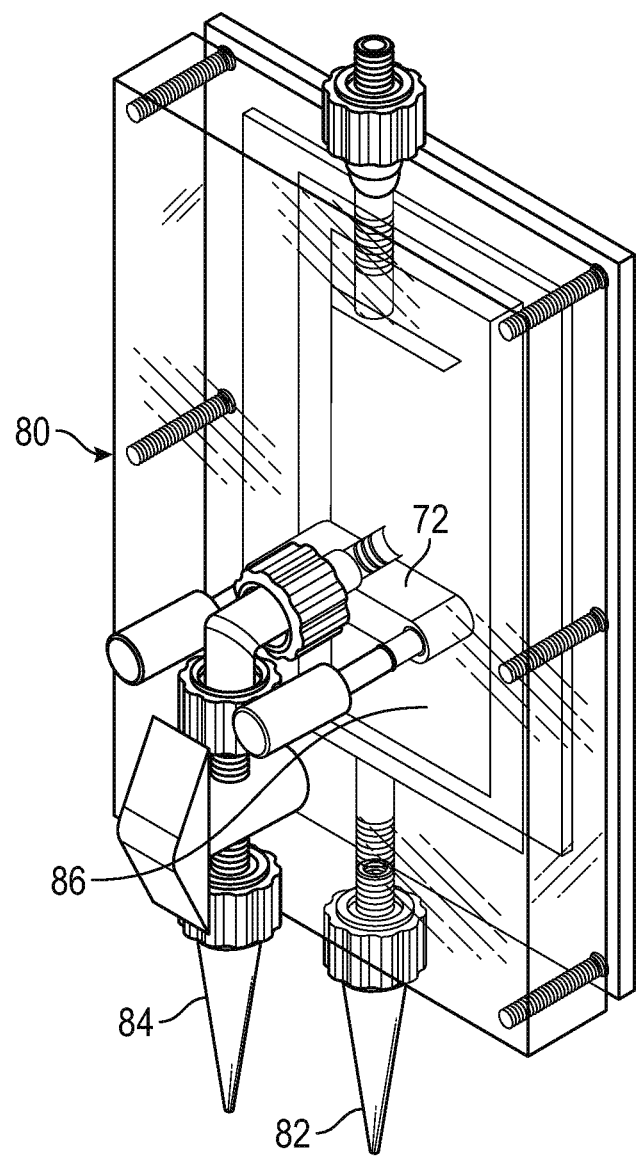
FIG. 7 is a perspective view of an alternative embodiment cartridge.
Figure 8:
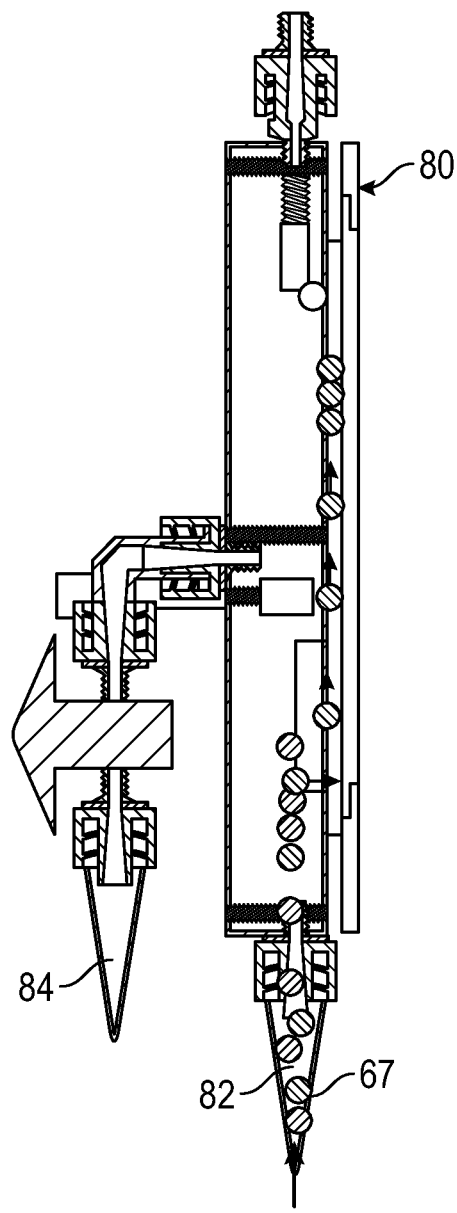
FIG. 8 is a side cross section view of the cartridge shown in FIG. 7 with solution drawn into the cartridge.
Figure 9:
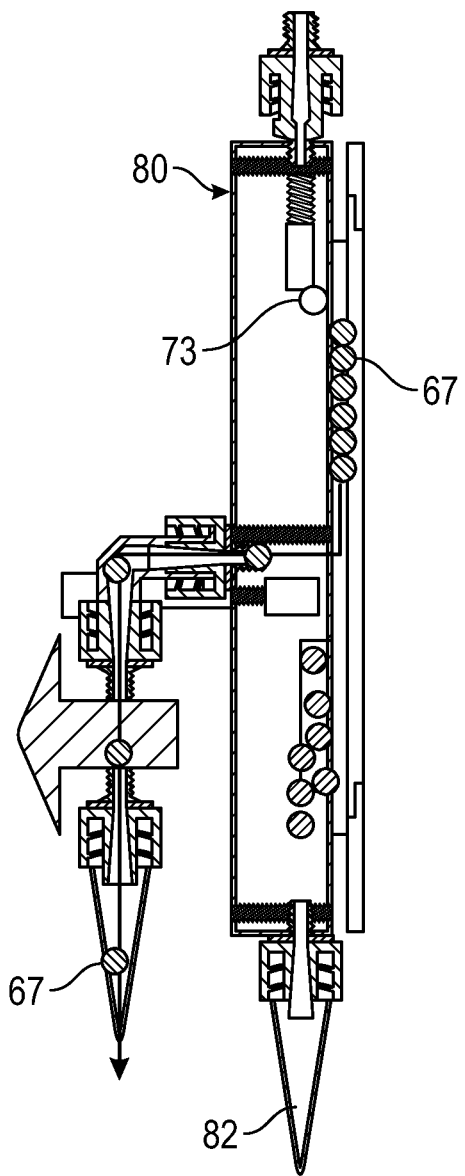
FIG. 9 is a side cross section view of the cartridge shown in FIG. 7 with magnetic bodies or cells in the solution now separated.

Turning to FIGS. 7-9, in an alternative cartridge 80, a sip tip 82 and an extraction tip 84 are provided on the bottom of the cartridge. The cartridge 80 is used in the vertical orientation shown to maximize purity of the extracted magnetic bodies. The sip tip 82 draws a solution sample into a loading chamber 86. The magnetic bodies are separated via a magnetic field as described above. After separation, the extraction gate 72 is closed and the magnetic bodies 67 are withdrawn from the cartridge through the extraction tip 84.

Figure 10:
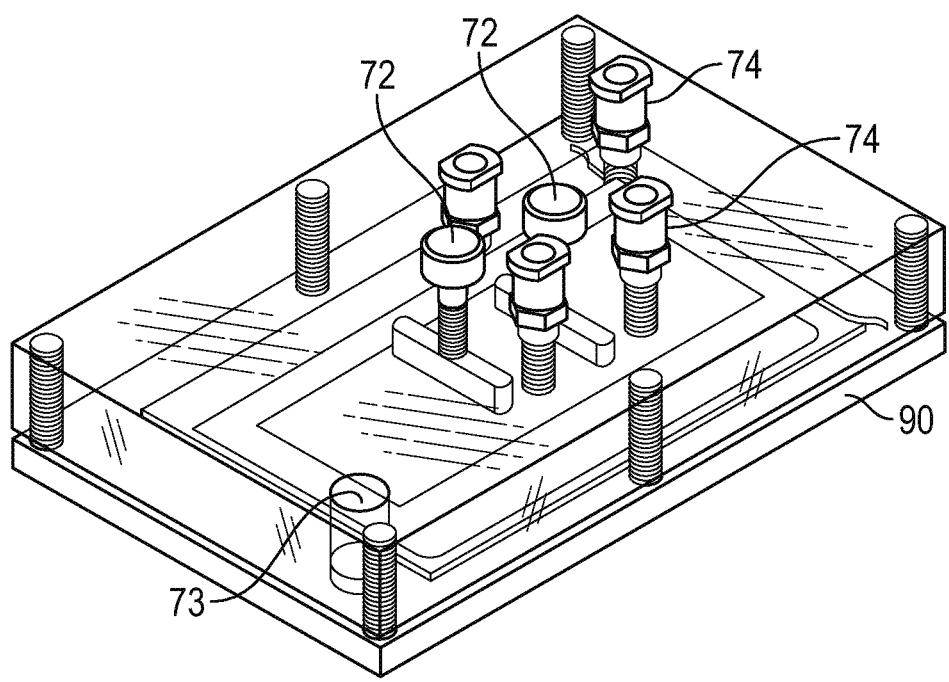
FIG. 10 is a perspective view of another alternative embodiment cartridge.

FIG. 10 shows another alternative cartridge 90 having an input well 73, two extraction gates 72 and two extraction ports 74 positioned to separate cells with different magnetization at specific pitch ranges, as discussed below. This allows the cartridge 90 to separate multiple cell populations. For example, the first extraction gate and the first extraction port may be positioned for extracting at pitches 12-30 while the second extraction gate and the second extraction port may be positioned for extracting at pitches 32-50 of the cartridge.

Figure 11A:
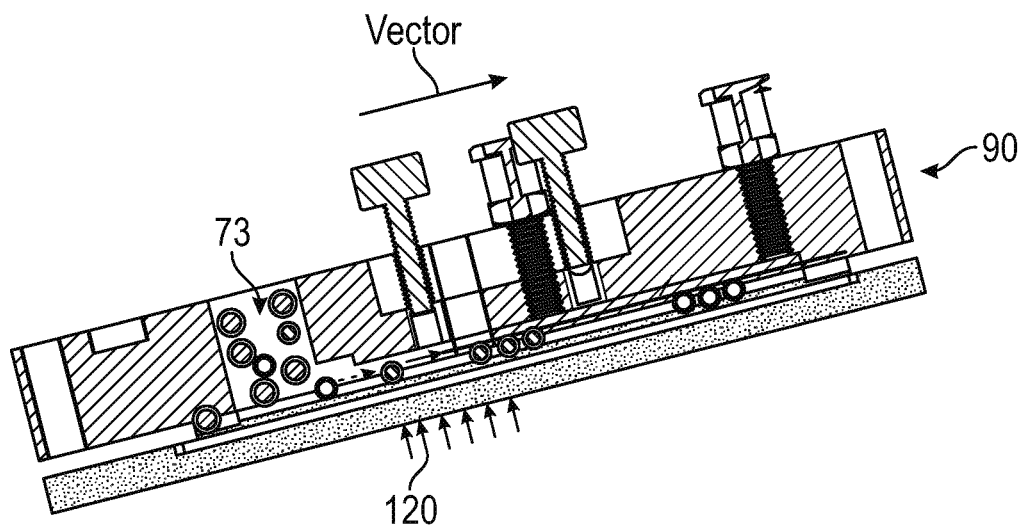
FIG. 11A is a side cross section view of the cartridge of FIG. 10 on an inclined angle with the solution introduced into the cartridge.
Figure 11B:
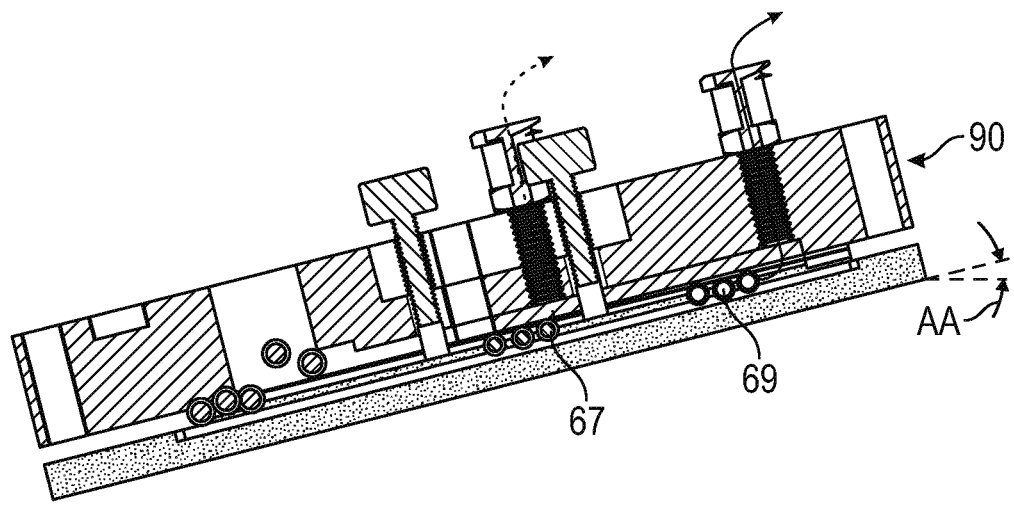
FIG. 11B is a side view of the cartridge of FIG. 11A with the magnetic bodies or cells now separated.

FIGS. 11A and 11B show the cartridge 90 operated at an inclined angle AA. Test results show separation of magnetic bodies with the substrate on an inclined angle is improved relative to a zero degree angle (with the magnetic substrate horizontal). Although angle AA may range from 0° to 90°, test results show higher ranges of 30, 45, 60 or 75 to 90° work well. A positive angle AA improves both purity and yield. This is a surprising outcome as gravity would not be expected to have such a large role with cell suspensions over short (10 minute) durations.

Figure 12:
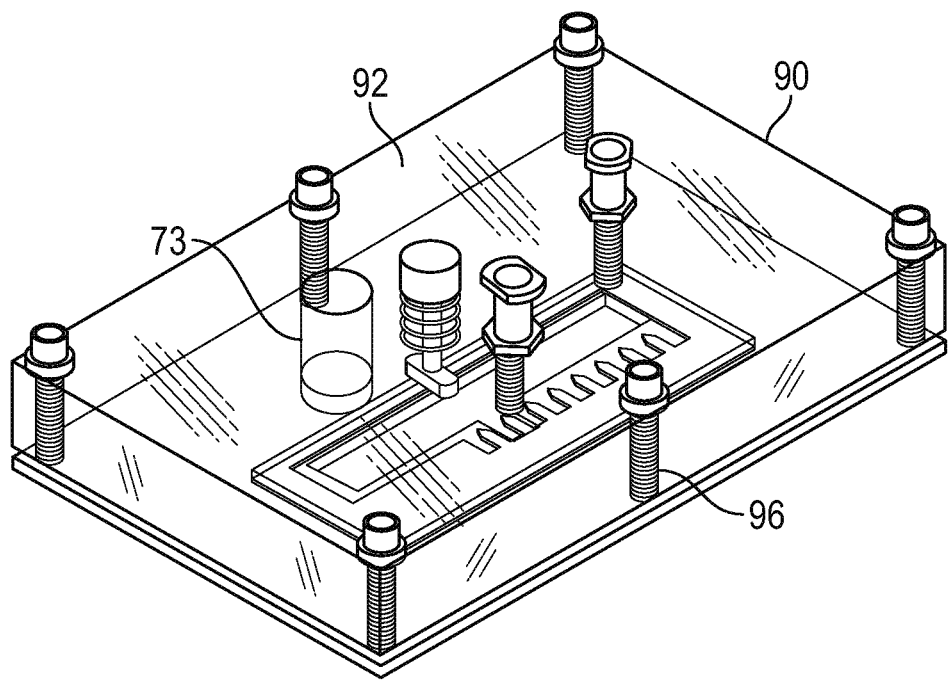
FIG. 12 is a perspective view of another alternative embodiment cartridge.
Figure 13:
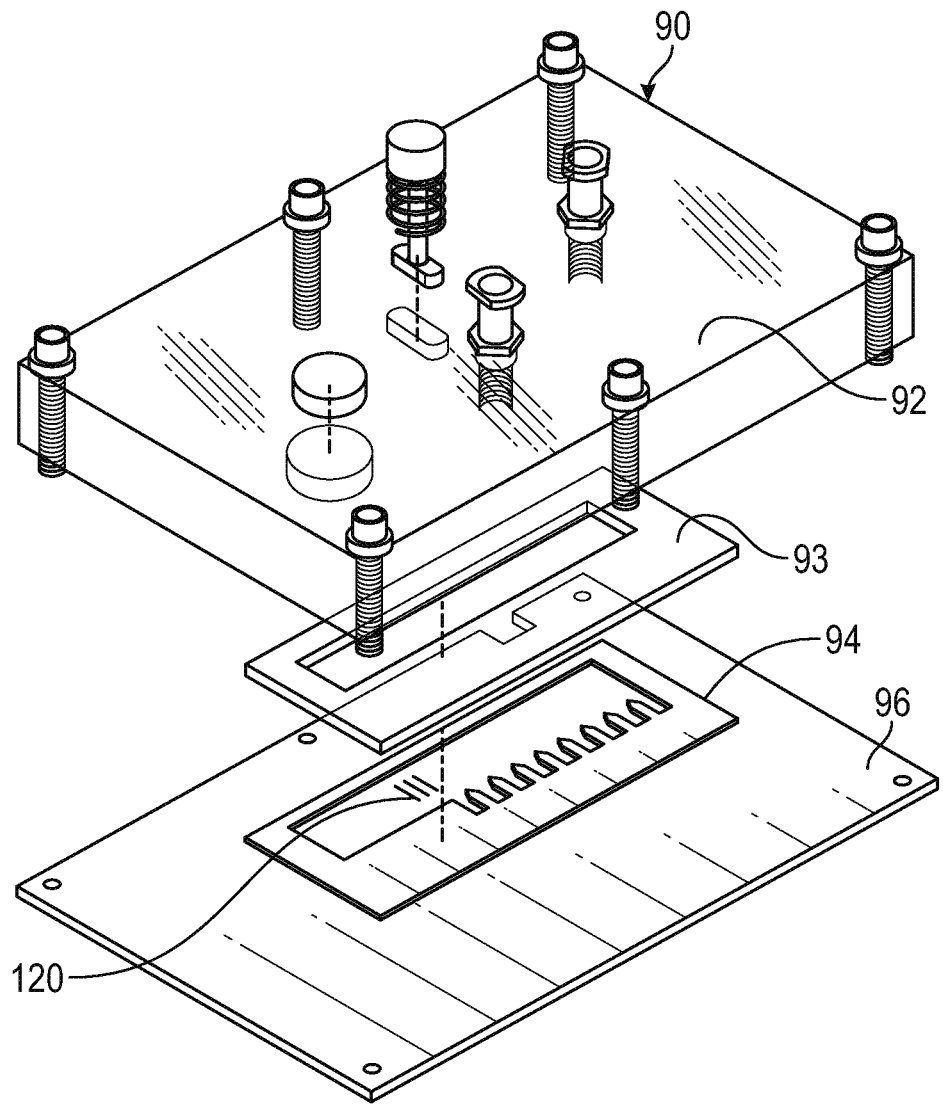
FIG. 13 is an exploded perspective view of the cartridge of FIG. 13.

FIGS. 12 and 13 show the cartridge 90 may be provided as a fluidic clamshell 92 with an optional gasket 93, a magnetic substrate 94 and a backing plate 96.

Figure 14:
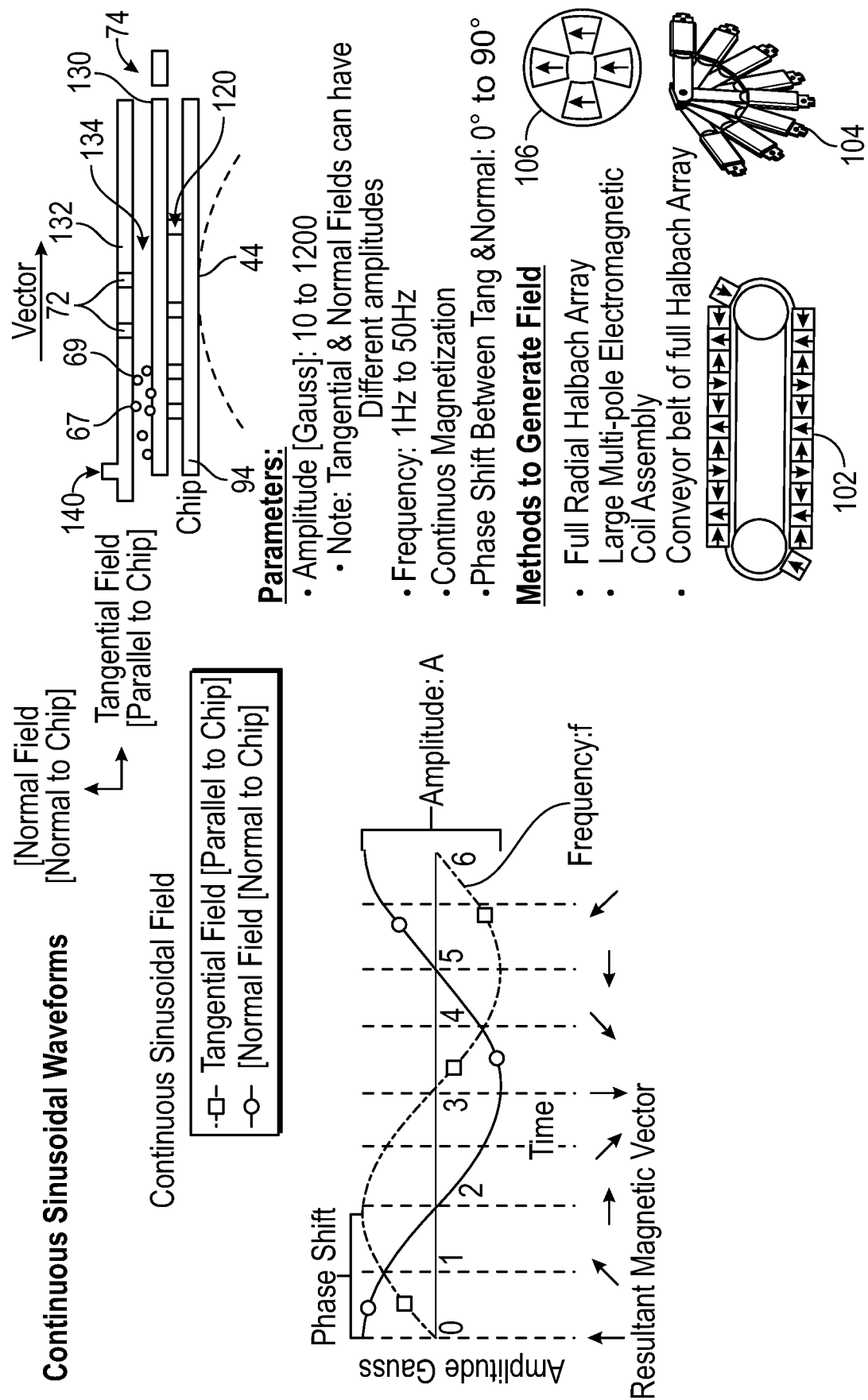

FIG. 14-17 show magnetic waveforms which may be generated by the magnetic field generator 44. The continuous sinusoidal magnetic field of FIG. 14 may have an amplitude of 10 to 1200 Gauss; frequency of 1 to 50 Hz; continuous magnetization; and a phase shift between Tangential and Normal of 0 to 90°. The tangential field (parallel to the magnetic substrate 94) and normal field (normal or perpendicular to the magnetic substrate) may have different amplitudes. FIG. 14 also shows an embodiment of the magnetic field generator 44 provided as a conveyor belt 102 of a full Halbach Array. The magnetic field generator 44 may also be provided as full radial Halbach Array 106, or a multi pole electromagnetic coil assembly 104. Each of these three types of magnetic field generator 44 may be used to generate the magnetic field of FIG. 14. Test results suggest that separating magnetic bodies is improved using an apparatus 30 having a full Halbach Array rather than a Partial Halbach Array. Using a full Halbach array may increase the intensity of magnetic flux density by 200% which increases throughput.

The continuous alternating poles magnetic field of FIG. 15 may have the same amplitude and frequency range as the magnetic field of FIG. 14. This magnetic field may be generated by a single magnetic wheel 108 or the belt 102.

A top 132 is spaced above a support surface 130 on top of the magnetic elements 120 providing a solution channel 134, as shown in FIG. 14. The support surface 130 may be a thin (e.g., 1 micron) conformal coating on the substrate. An input channel or tube 140 may be provided on the top 132 leading into a chamber between the top and the support surface, to input solution into the substrate 94.

Figure 16:
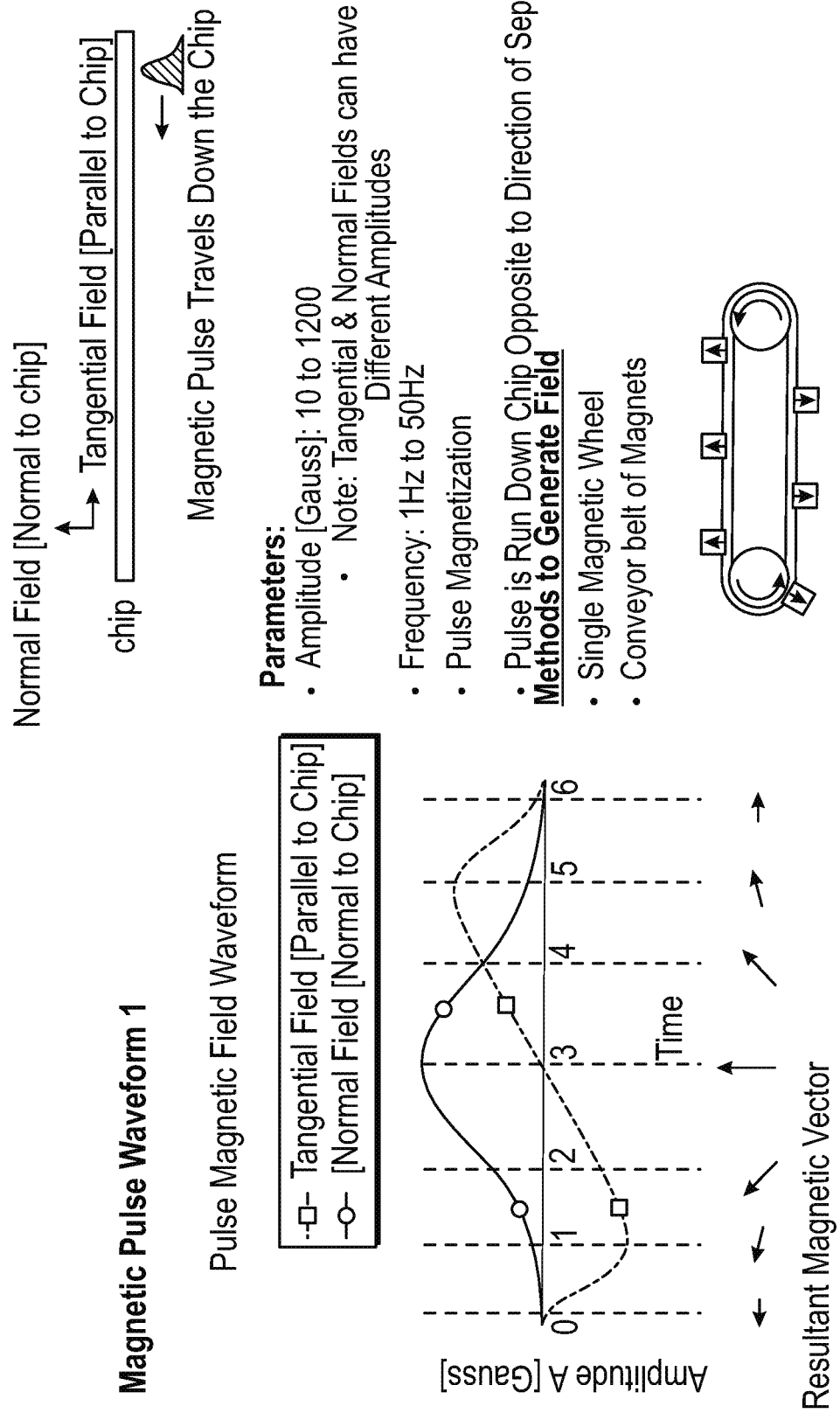
Figure 17:
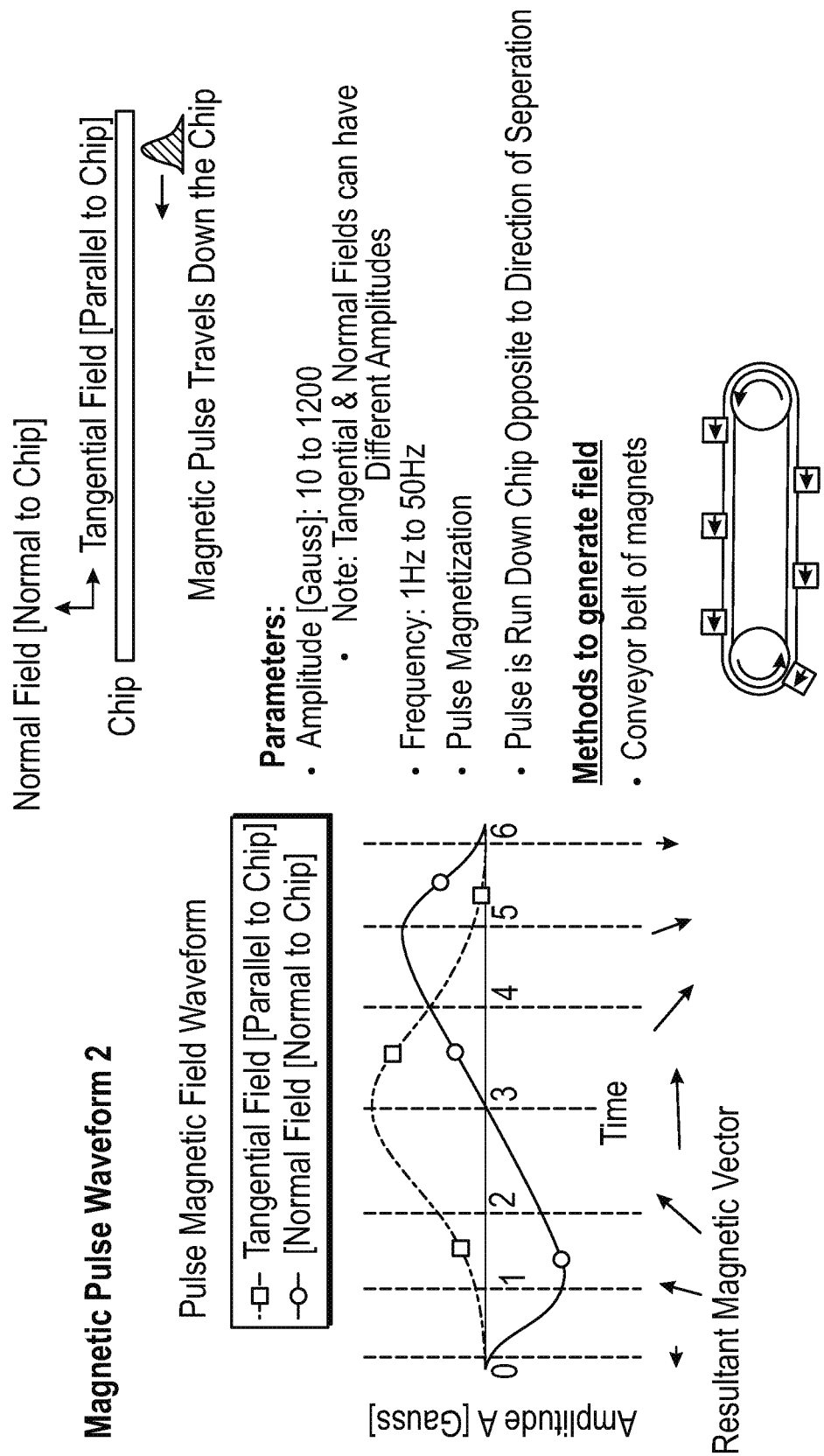

FIGS. 16 and 17 show magnetic pulse waveforms that may also optionally be used. These may be generated by the conveyor belt 102.

Figure 18A:
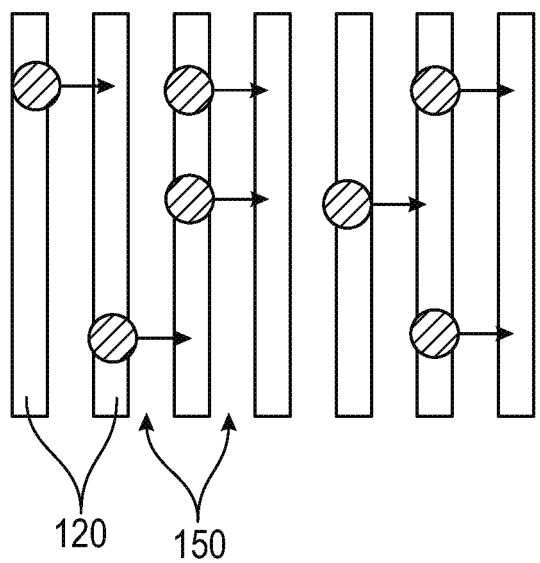
FIG. 18A is a schematic view of an arrangement of magnetic bars which may be used in any of the cartridges.

Each of the cartridges 60 has a magnetic substrate 94 having a vector of magnetic elements or bars 120, as shown in FIG. 18A. The pitch spacing or gap 150 between adjacent magnetic bars 120 may progressively increase from the low end to the high end of the substrate to provide improved one dimensional magnetic ratcheting. Each gap 150 may be about 2 μm to about 10 μm wider than the previous gap in the vector direction indicated by the arrow in FIG. 18A. A typical substrate pitch (center to center distance of bars) may range from 10 μm to 100 μm depending on the location within the substrate. However, the pitch increment level can also vary. These are two separate parameters: "Element Pitch" which generally ranges from 10 to 100 μm and "Pitch Increment" which generally ranges from 2 um to 10 um. As an example, a substrate have 20 pitch zones or groups of spaced apart magnetic bars, with each pitch zone spanning e.g., 2 mm. In the first pitch zone the magnetic bars are spaced apart with a pitch of 10 microns. The adjacent or adjoining second or next pitch zone, has magnetic bars spaced apart with a pitch of 12 microns, the third pitch zone having magnetic bars spaced apart with a pitch of 14 microns, etc., with the pitch of each pitch zone progressively increasing by 2 microns, up to an ending pitch of 50 μm. In another example, the first pitch zone has a starting pitch of 10 μm, the second pitch zone has a 20 micron pitch, etc., up to a final pitch of 100 μm (i.e., pitches of 10, 20, 30, 40 . . . 100 microns.)

Figure 19:
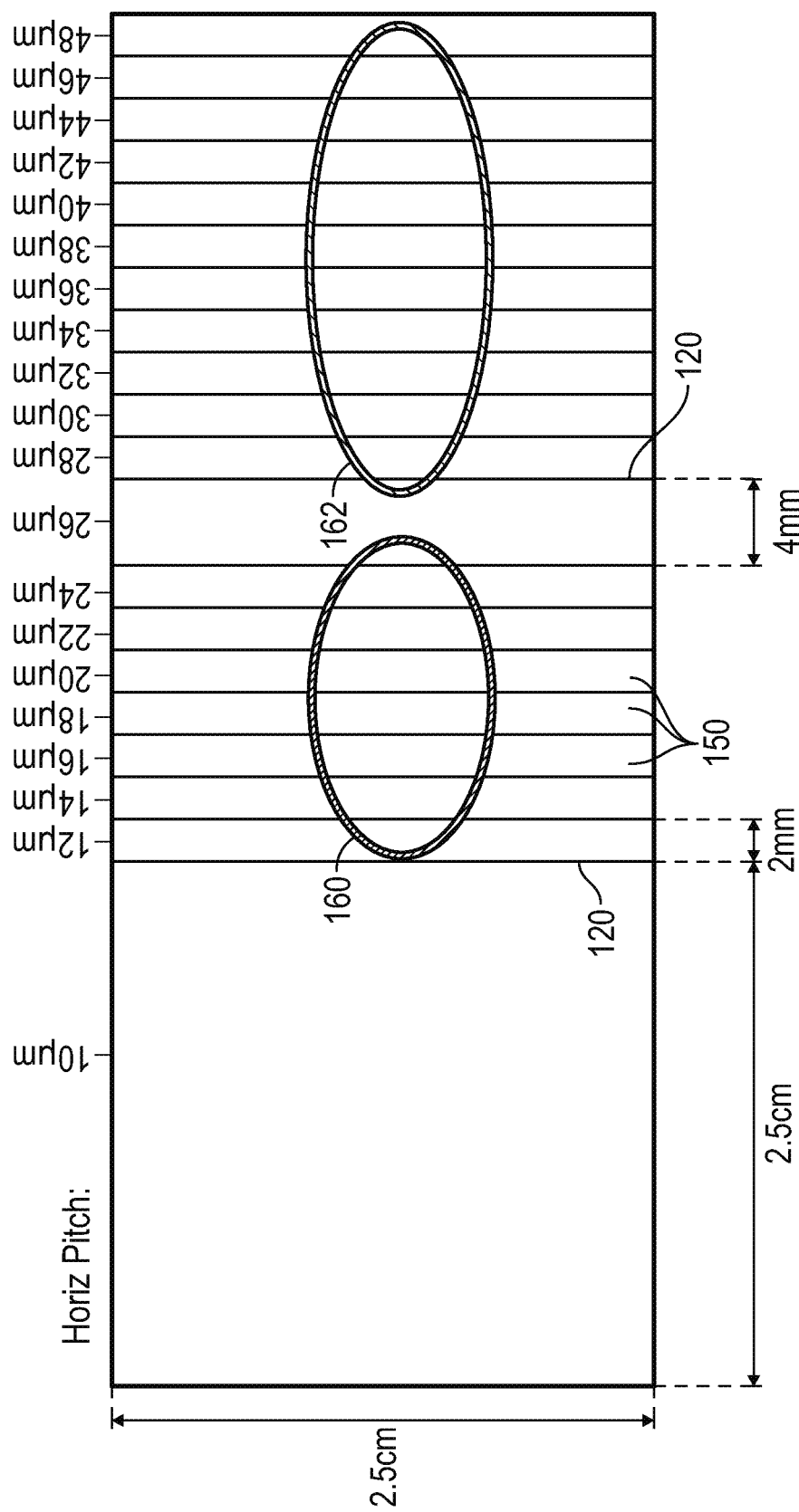
FIG. 19 is a schematic view of pitch spacing of the magnetic bars of FIG. 18A.

Examples of pitch spacing are shown in FIG. 19. The substrate may be conceptually divided into pitch zones 160 and 162. The magnetic bars may be made of a magnetically soft alloy such as $Ni_xFe_y$, $Ni_xMo_yFe_z$, $Cu_xMn_yAl_z$, $Cu_xMn_yIn_z$, $Cu_xMn_ySn_z$, $Ni_xMn_yAl_z$, $Ni_xMn_yIn_z$, $Ni_xMn_ySn_z$, $Ni_xMn_ySb_z$, $Co_xMn_yAl_z$, $Co_xMn_ySi_z$, $Co_xMn_yGa_z$, $Co_xMn_yGe_z$, $Pd_xMn_yAl_z$, $Pd_xMn_yIn_z$, $Pd_xMn_ySn_z$, $Pd_xMn_ySb_z$, $Fe_xNi_yCo_z$, $Cu_xNi_yFe_z$, and/or $Fe_vNi_wAl_xCo_yCu_z$.

Figure 18B:
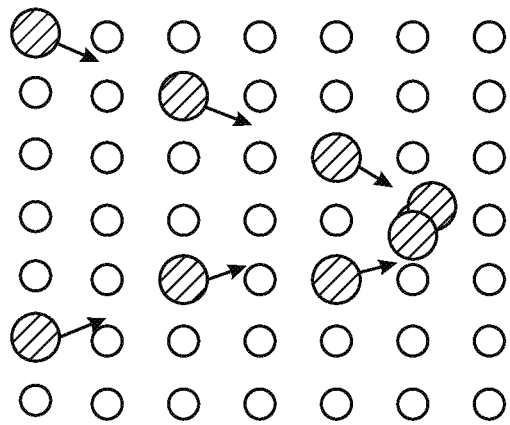
FIG. 18B is a schematic view of a prior art pillar design.

Using a cartridge 60 having a magnetic substrate 94 with a single vector of bars 120 rather than a matrix of pillars in columns and rows as shown in FIG. 18B provides improved results. The single vector of bars 120 of FIG. 18A surprisingly reduces or avoids the cell clogging observed with the array/matrix of FIG. 18B. The pillar design of FIG. 18B is more sensitive to in-plane magnetic field bias. This can cause cells to transport and eventually aggregate as they crash into each other. Cell aggregates can skew the magnetic separation quality as cell aggregates have much different magnetic ratcheting transport behavior. For example, if a cell with low signal (few magnetic beads) aggregates with a cell with high signal (lots of magnetic beads) the aggregate will move to a high pillar pitch which can decrease target cell purity.

A 1:1 Height:width for small features (5-20 microns) is significant as other aspect ratios ("Pancakes" or "Poles") do not generate the type of field needed for effective separations. Since each magnetic bar 120 amplifies the externally applied magnetic field from the magnetic field generator 44, a higher density of magnetic bars increases the magnetic energy density per square centimeter of substrate. A higher magnetic energy per square centimeter yields higher throughput because cells can be transported faster across the substrate compared to a lower magnetic element fill factor. A similar concept applies in conductivity. Higher magnetic fill enables larger amplification of applied magnetic fields, similar to doping in silicon wafers.

Separating results may be improved by selecting magnetic beads on the basis of iron content rather than bead size. Separations are not restricted to cells with magnetic beads bound to external surface marker antigens, but by live cell populations with differential ability to internalize iron containing beads. Although the description above refers primarily to cells, the apparatus and methods described apply as well for use with other types of particles.

Figure 20:
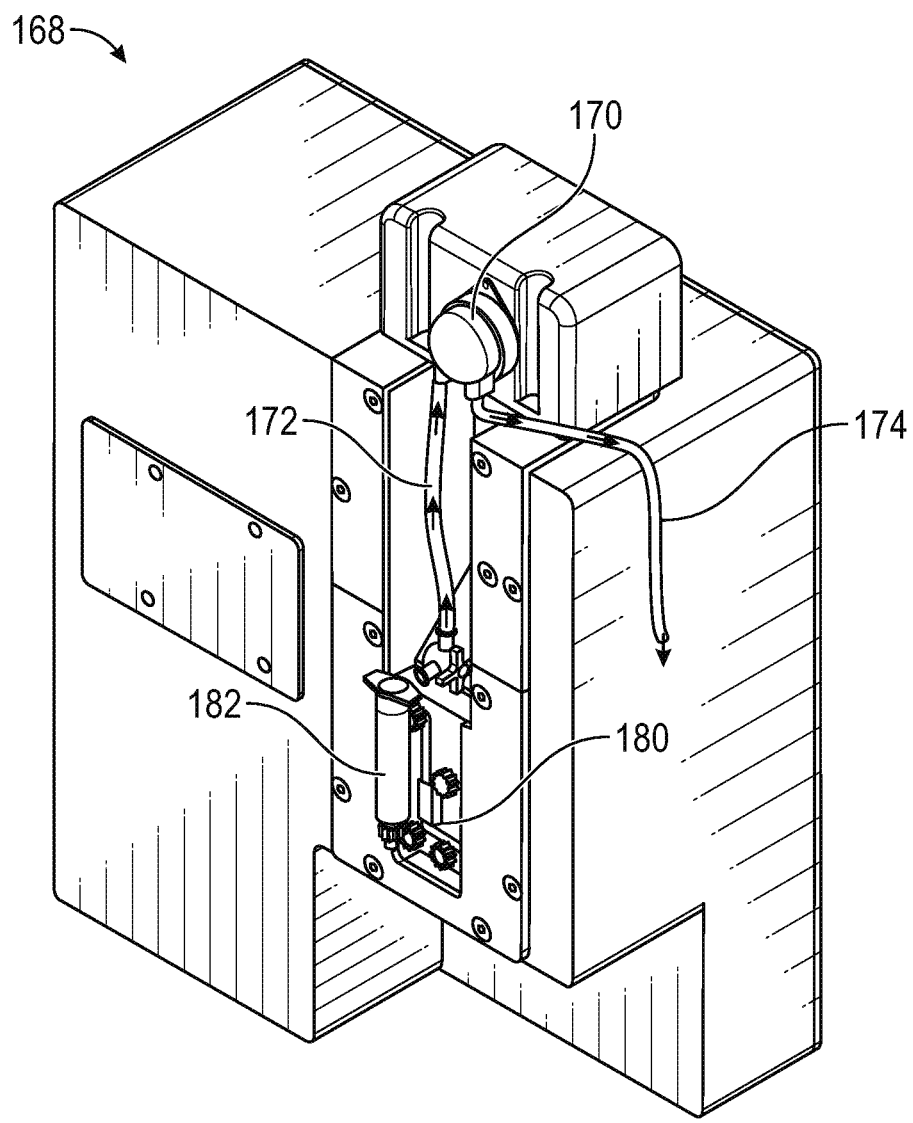
FIG. 20 is a perspective view of an alternative magnetic ratcheting apparatus.
Figure 21:
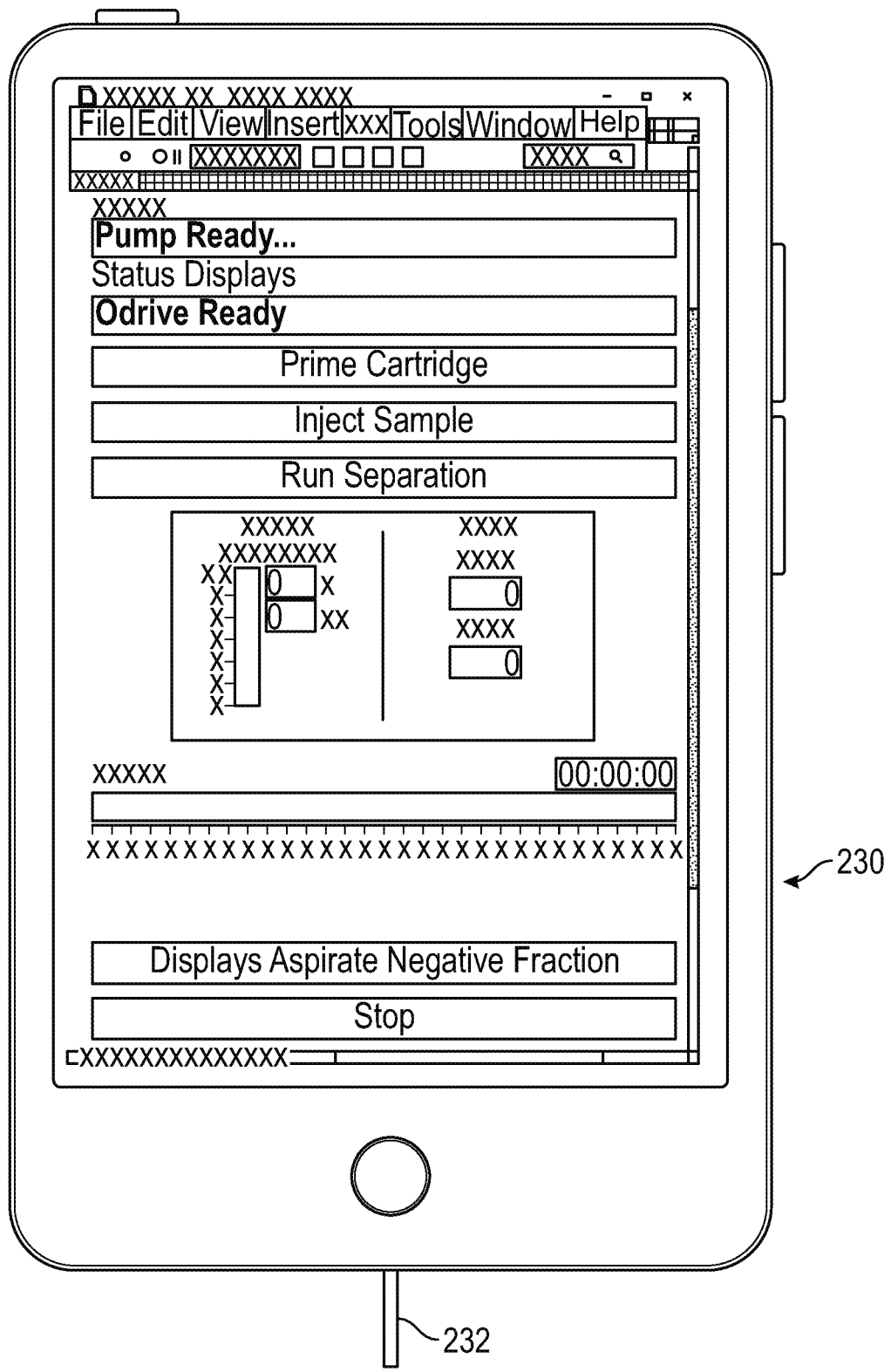
FIG. 21 is a front view of device that may be used to control the magnetic ratcheting apparatus shown in FIGS. 1 and 20.
Figure 22:
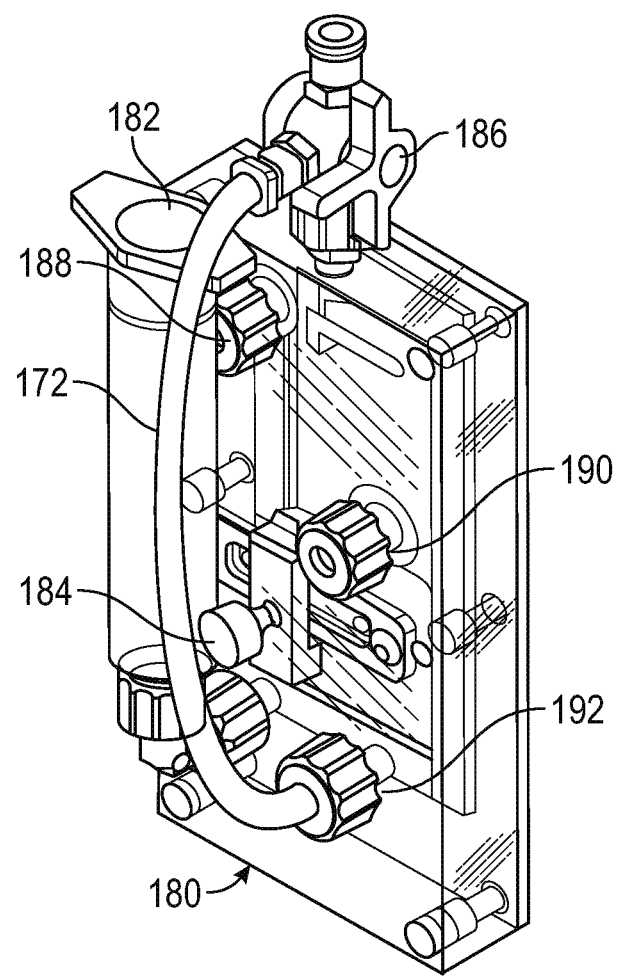
FIG. 22 is a perspective view of an alternative cartridge for performing magnetic ratcheting.

FIGS. 20-22 show an alternative apparatus 168 having a pump 170, such as a peristaltic pump, for moving liquid out of an alternative cartridge 180. A pump tube 172 connects the pump inlet to a valve 186 on the cartridge 180 shown in FIG. 22. The outlet of the pump 170 is connected to a waste tube 174 leading to a drain or waste container. Referring to FIG. 22, the cartridge 180 may be constructed with a backing plate attached to a cartridge body and the ferromagnetic chip on a gasket or adhesive spacer as described above relative to the cartridge shown in FIGS. 4A04C. The cartridge 180 has a sample reservoir 182, which may be provided as a syringe body. The cartridge includes an extraction lock gate valve 184, a cell washing port 188, a cell extraction port 190 and a waste outlet port 192.

Figure 23D:
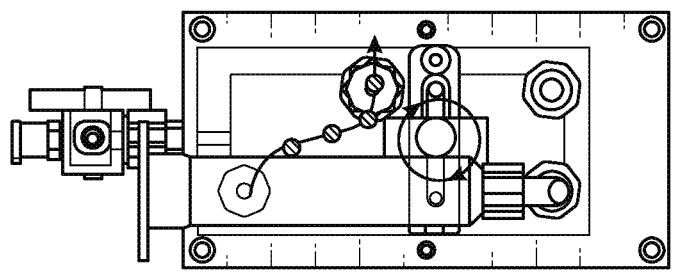
FIGS. 23A-23D are front views of the cartridge of FIG. 22 showing a sequence of operations.
Figure 23C:
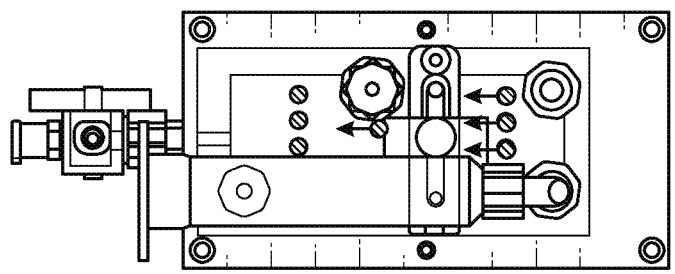
Figure 23B:
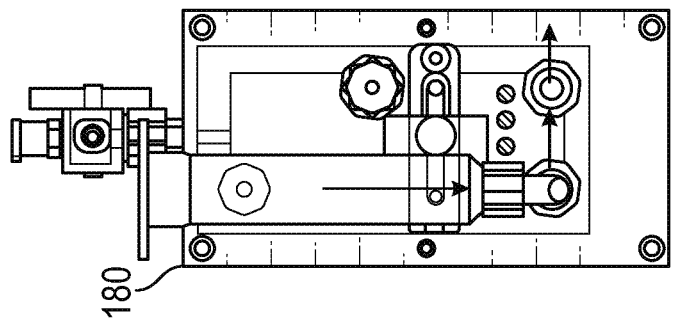
Figure 23A:
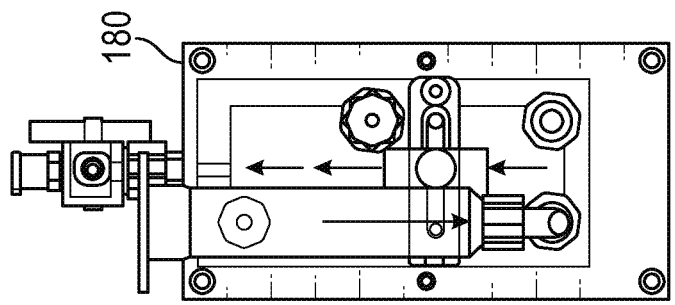

Referring to FIGS. 23A to 23D, in use the cartridge 180 is primed with a buffer solution. With the valve 186 is in the first position as shown in FIG. 22, the pump 170 draws buffer solution from the reservoir 182 into the cartridge, as shown in FIG. 23A. Next, the valve 186 is moved into a second position and the pump is turned on to draw a sample into the cartridge 180. Magnetic cells are captured and magnetic ratcheting is performed as described above, as shown in FIGS. 23B and 23C. The extraction lock 184 is then closed isolating the extracted cells or particles and they are eluted from the cartridge 180 via the cell extraction port 190, as shown in FIG. 23D.

FIG. 21 shows a tablet or similar device 230 having a user interface for controlling the analyzer 168. The device 230 is connected to the analyzer 168 via a cable 232 or a wireless connection. The device may also display operating parameters and status of the analyzer. In one embodiment, the device 230 may display the status of the analyzer 168, as well as liquid volumes moved into an out of the cartridge. Other data, such as duration of a separation step may also be displayed. The analyzer 168 may be controlled via the touchscreen of the device 230 which may include touch icons for e.g., the steps of priming the cartridge, injecting a sample, separating the sample, and aspirating liquid from the cartridge or reservoir. Operation of the pump and the valves of the cartridge may be automated via actuators or motors to provide for automated operation of the analyzer 168.

Figure 24:
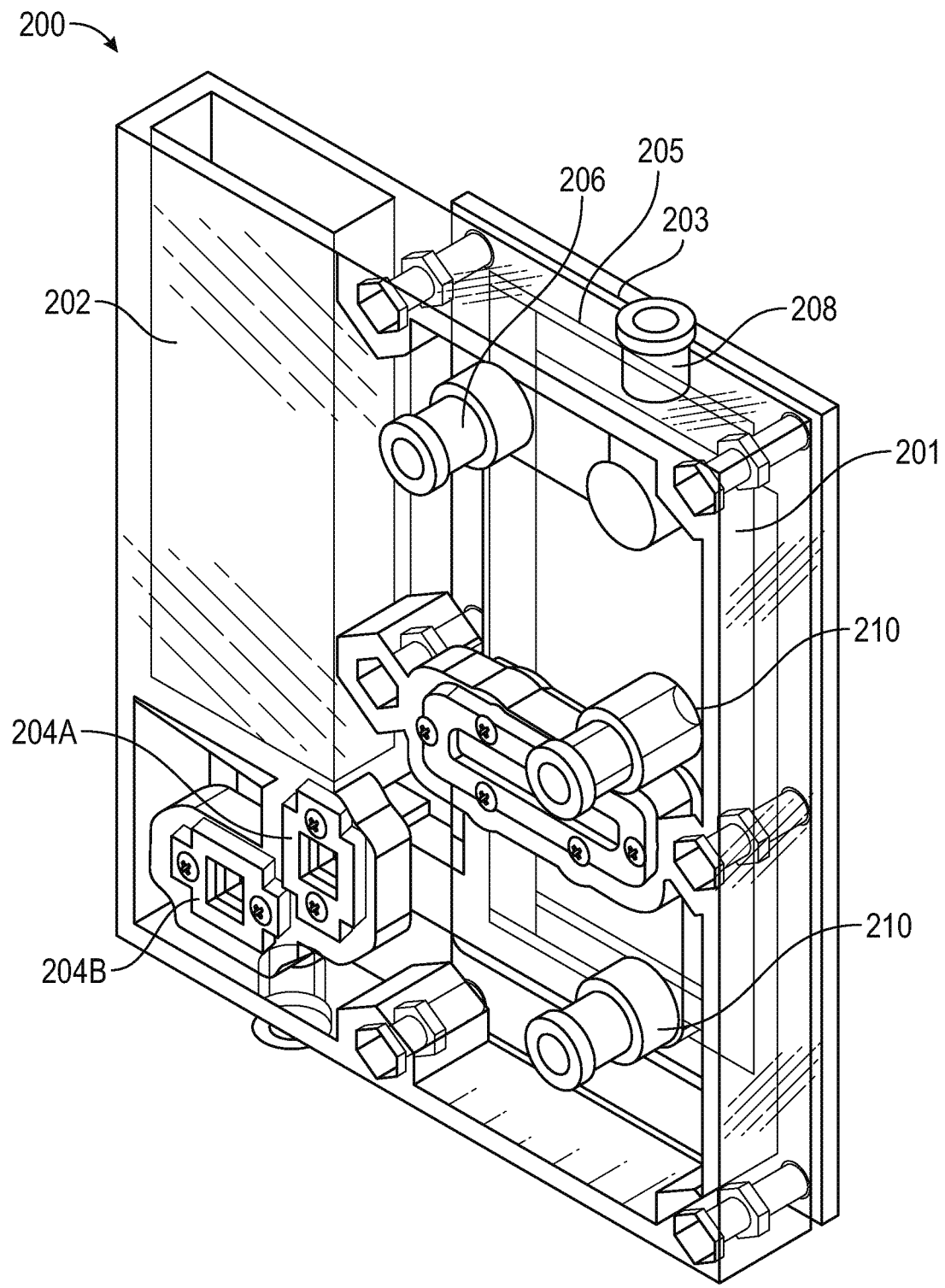
FIG. 24 is a perspective view of another alternative cartridge for performing magnetic ratcheting.
Figure 25D:
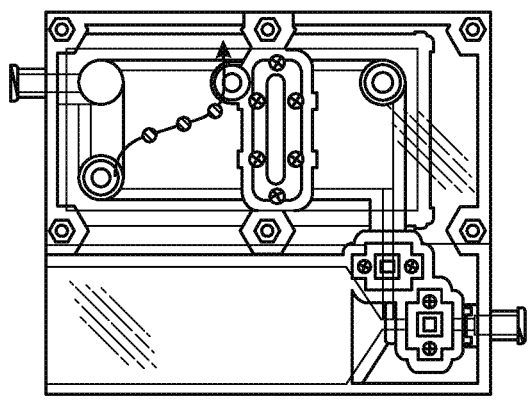
FIGS. 25A-25D are front views of the cartridge of FIG. 24 showing a sequence of operations.
Figure 25C:
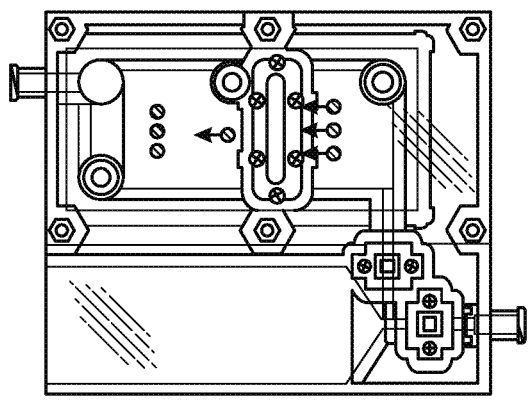
Figure 25B:
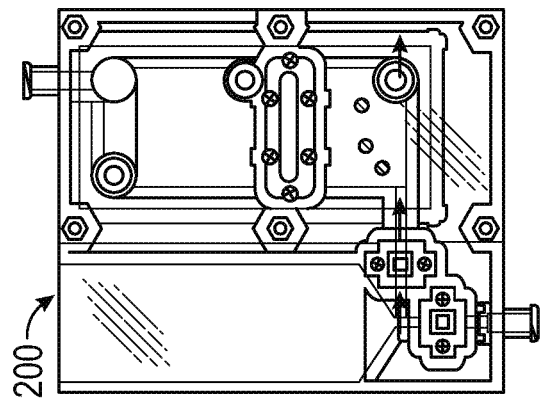
Figure 25A:
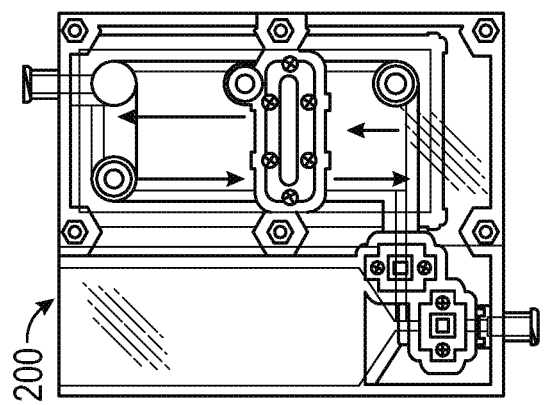

FIG. 24 shows another alternative cartridge 200 having a cartridge body backing plate 203 screwed onto a cartridge body 201, holding a ferromagnet chip 205 within the cartridge 200. A sample reservoir 202 is formed within the cartridge body 201. First and second flexible gate valves 204A and 204B provide for sample injection, and for the sample reservoir. A buffer port 206, a fluid pumping port 208 and cell removal ports 210 provide fluid connections to for movement of liquid into and out of the cartridge. The cartridge 200 may be used as described above and as shown in FIGS. 25A to 25D.

The substrate may be manufactured by applying a metal layer onto glass, etching the magnetic bar pattern using photolithography and then metal plating. As used here, reference to cells also includes other microscopic particles or bodies.

Thus, novel apparatus, devices and methods have been shown and described. Various changes and substitutions can of course be made without departing from the spirit and scope of the invention. The invention, therefore, should not be limited, except by the following claims, and their equivalents.

The invention claimed is:

1. A system for magnetic separation of magnetic bodies comprising:
   a substrate;
   a plurality of ferromagnetic elements spaced apart in pitch zones on the substrate, with the spacing between adjacent ferromagnetic elements increasing in a direction along a vector of ferromagnetic elements, and the increase in spacing between adjacent ferromagnetic elements is within a range of 10 μm to 100 μm;
   a support surface over the ferromagnetic elements;
   a magnetic field generator disposed adjacent to the support surface, the magnetic field generator configured to generate a continuously rotating sinusoidal magnetic field;
   a channel over the support surface; and
   a plurality of extraction gates aligned over the pitch zones, the extraction gates movable to open or close off the channel to separate magnetic or non-magnetic bodies in a plurality of ranges.

2. The system of claim 1 wherein the magnetic field generator comprises a rotating wheel having a plurality of permanent magnets arranged in a full radial Halbach array.

3. The system of claim 1 wherein the ferromagnetic elements comprise spaced apart bars of a magnetically soft alloy selected from the group consisting of $Ni_xFe_y$, $Ni_xMo_yFe_z$, $Cu_xMn_yAl_z$, $Cu_xMn_yIn_z$, $Cu_xMn_ySn_z$, $Ni_xMn_yAl_z$, $Ni_xMn_yIn_z$, $Ni_xMn_ySn_z$, $Ni_xMn_ySb_z$, $Co_xMn_yAl_z$, $Co_xMn_ySi_z$, $Fe_xNi_yCo_z$, $Cu_xNi_yFe_z$, and/or $Fe_xNi_wAL_xCo_yCu_z$.

4. The system of claim 1 wherein the channel is between the support surface and a top, further including an input well leading into the channel.

5. The system of claim 1 wherein the extraction gates confine magnetic or non-magnetic bodies within specified ferromagnetic pitch ranges.

6. The system of claim 1 wherein the substrate is flat and maintained at an inclined angle to gravity.

7. The system of claim 1 wherein the ferromagnetic elements comprise bars disposed on the substrate in a single row.

8. The system of claim 1 wherein each extraction gate is associated with an extraction port.

9. The system of claim 1 wherein the substrate comprises glass and the ferromagnetic elements comprise bars of a metal layer on the glass, the bars perpendicular to a length of the substrate.

10. The system of claim 1 wherein the substrate is inclined at an angle between horizontal and vertical.

11. The system of claim 1 wherein the substrate is inclined at an angle of from 30 to 75 degrees.

12. A system for magnetic separation of magnetic particles or cells comprising:
   a rigid substrate;
   a plurality of ferromagnetic elements spaced apart in a row in pitch zones on the substrate;
   a support surface disposed over the ferromagnetic elements;
   a channel over the support surface;
   an extraction gate aligned over each of the pitch zones, the extraction gates movable to open or close off the channel;
   a magnetic field generator providing a rotating magnetic field at the support surface, the magnetic field generator comprising a rotating wheel having a plurality of permanent magnets arranged in a full radial Halbach array; and
   the substrate having a non-zero angle orientation relative to gravity.

13. The system of claim 12 wherein the spacing between the ferromagnetic elements increases from a lower end of the substrate towards a higher end of the substrate.

14. The system of claim 12 wherein the ferromagnetic elements comprise bars disposed on the substrate.

15. The system of claim 12 wherein all of the ferromagnetic elements lie in a plane having a non-zero angle relative to gravity.

16. A system for magnetic separation of magnetic particles or cells comprising:
   a substrate;
   a plurality of magnetic bars spaced apart on the substrate in a single row, the magnetic bars forming a plurality of pitch zones;
   a support surface disposed over the magnetic bars;
   a channel over the support surface;
   an extraction gate aligned over each pitch zone, each extraction gate movable to open or close off a portion of the channel; and
   a magnetic field generator for applying a rotating magnetic field to the support surface.

17. The system of claim 16 wherein the substrate is oriented between horizontal and vertical relative to gravity.

18. The system of claim 16 wherein all of the magnetic bars lie in a plane having a non-zero angle relative to gravity.

19. The system of claim 16 wherein the substrate is an angle of from 30 to 75 degrees relative to gravity.

* * * * *